US012622688B2

(12) United States Patent
Dale et al.

(10) Patent No.: US 12,622,688 B2
(45) Date of Patent: May 12, 2026

(54) METHODS AND DEVICE FOR CLOSURE OF A TISSUE DEFECT

(71) Applicant: St. Jude Medical, Cardiology Division, Inc., St. Paul, MN (US)

(72) Inventors: Theodore Dale, Corcoran, MN (US); Tracee Eidenschink, Wayzata, MN (US); Linda Cornelius, Wayzata, MN (US); Caytlin Gale, Minneapolis, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 9 days.

(21) Appl. No.: 18/816,831

(22) Filed: Aug. 27, 2024

(65) Prior Publication Data

US 2025/0090159 A1     Mar. 20, 2025

Related U.S. Application Data

(60) Provisional application No. 63/583,493, filed on Sep. 18, 2023.

(51) Int. Cl.
*A61B 17/04* (2006.01)
*A61B 17/00* (2006.01)

(52) U.S. Cl.
CPC .................... *A61B 17/0401* (2013.01); *A61B 2017/00623* (2013.01)

(58) Field of Classification Search
CPC ...... A61B 17/0401; A61B 2017/00623; A61B 2017/00575; A61B 2017/00592; A61B 2017/00867; A61B 17/0057
See application file for complete search history.

(56) References Cited

U.S. PATENT DOCUMENTS

| | | | |
|---|---|---|---|
| 2003/0208209 A1 * | 11/2003 | Gambale ............ | A61B 17/0482 |
| | | | 606/144 |
| 2007/0032796 A1 * | 2/2007 | Chin-Chen ........ | A61B 17/0057 |
| | | | 606/139 |
| 2010/0114140 A1 * | 5/2010 | Chanduszko ...... | A61B 17/3468 |
| | | | 606/185 |
| 2012/0116418 A1 * | 5/2012 | Belson ............... | A61B 17/3403 |
| | | | 606/139 |
| 2016/0338706 A1 | 11/2016 | Rowe | |

* cited by examiner

*Primary Examiner* — Richard G Louis
(74) *Attorney, Agent, or Firm* — SLEMAN & LUND LLP

(57) ABSTRACT

A coiled needle and deployment methods of the same are disclosed herein. The coiled needle includes a coiled body with one or more complete turns and at least one sharp end. The coiled needle may be used to close a patent foramen ovale (PFO) by advancing the coiled needle to a location adjacent to the PFO, positioning a first end of the coiled needle against tissue adjacent to the PFO, puncturing the tissue with the first end of the coiled needle, and rotating the coiled needle to advance the coiled needle through tissue of both a septum primum and a septum secundum defining the PFO. PFO closure systems and suture delivery systems including such coiled needles are further described.

16 Claims, 10 Drawing Sheets

METHODS AND DEVICE FOR CLOSURE OF A TISSUE DEFECT

CROSS-REFERENCE TO RELATED APPLICATIONS

This application claims the benefit of priority to U.S. Provisional Patent Application No. 63/583,493, filed on Sep. 18, 2023, the entire contents of which are hereby incorporated by reference herein.

BACKGROUND OF THE DISCLOSURE

A. Field of Disclosure

The present disclosure relates generally to medical devices that are used in the human body and methods of operating the same. In particular, the present disclosure is directed to a medical device for closure of a tissue defect, such as an atrial tissue defect, and methods of operating and deploying the same.

B. Background

An occluding device (or "occluder") is a medical device used to treat tissue at a target site within the human body, such as an abnormality, a vessel, an organ, an opening, a chamber, a channel, a hole, a cavity, a lumen, or the like. For example, an occluder may be used for treating atrial septal defects (ASDs). Atrial septal defects are common congenital heart defects that allow blood to flow between the left and right atria of the heart, decreasing cardiac output.

Although ASDs come in many forms, one example type of ASD is conventionally referred to as a patent foramen ovale, or PFO. In PFOs, a tunnel within the atrial tissue is formed, such as during fetal development, between the left and right atria. PFOs may vary in severity from generally benign to those warranting surgical intervention, such as via implantation of an occluding device, which may be implanted in the heart to repair the PFO.

In addition to PFO interventions, other percutaneous procedures are becoming more prevalent in surgical practice as well, including those for treating a variety of atrial septal defects, including as described above, but not limited to, PFOs. Conventional devices for closing ASDs include, for example, occlusive devices formed from a braided mesh material.

However, future surgical access to left and/or right atria of the heart may be limited or otherwise made more difficult by the implantation of these braided occluding devices. In addition, implantation of some known occluders and other ASD treatment devices may also, in some cases, result in erosion of surrounding tissue and/or other disruption to the conduction system of the heart.

Accordingly, it would be desirable to close an ASD, such as a PFO, with an alternate closure device or system.

SUMMARY OF THE DISCLOSURE

The present disclosure is directed to a method of closing a patent foramen ovale (PFO), the method including: (i) advancing a coiled needle to a location adjacent to the PFO, (ii) positioning a first end of the coiled needle against tissue adjacent to the PFO, (iii) puncturing the tissue with the first end of the coiled needle, and (iv) rotating the coiled needle to advance the coiled needle through tissue of both a septum primum and a septum secundum defining the PFO.

The present disclosure is also directed to a PFO closure system including a closure device including a body extending between a first end and a second end, the body having a coiled shape including more than one complete turn. At least one of the first end or the second end is a sharp point configured to puncture tissue at a target site within anatomy of a patient. The PFO closure system also includes a delivery device for delivering the closure device to the PFO.

Additionally, a suture delivery system as described herein includes a coiled tube having a hollow coiled body defining a lumen therethrough, a first end, and a second end, the first end including a sharp point configured to puncture tissue at a target site within anatomy of a patient.

BRIEF DESCRIPTION OF THE DRAWINGS

FIG. 10 depicts a medical device in accordance with the present disclosure including a coiled needle and a suture coupled thereto.

Corresponding reference characters indicate corresponding parts throughout the several views of the drawings. It is understood that Figures are not necessarily to scale.

DETAILED DESCRIPTION OF THE DISCLOSURE

Figure 1:
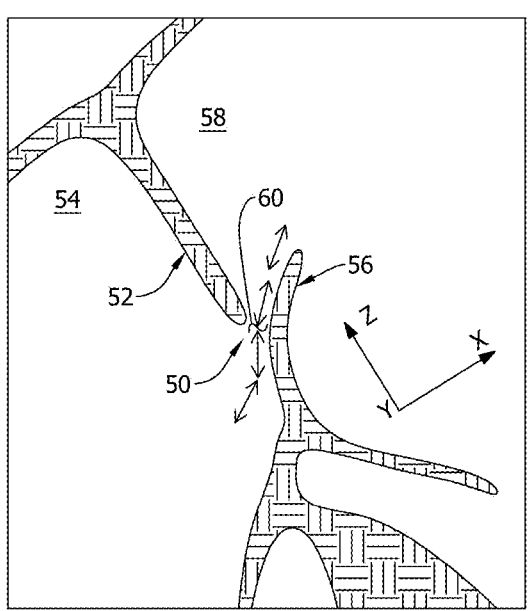
FIG. 1 is a simplified diagram of a patent foramen ovale (PFO).

The present disclosure relates generally to medical devices that are used in the human body. Specifically, the present disclosure provides medical devices including metallic coils, non-metallic coils, sutures, and combinations thereof, for treatment of an atrial septal defect (ASD), such as a patent foramen ovale (PFO). The medical devices of the present disclosure enable closure of the ASDs without deployment of an occlusive device.

In particular, the present disclosure is directed to a coiled or spiral needle that closes a PFO to facilitate proper blood flow within the heart while reducing an amount of material (e.g., providing a device without braided-web discs) to provide such closure. In some embodiments, the coiled needle is itself deployed in the tissue and retained thereat to close the PFO. In other embodiments, the coiled needle is used as a delivery component to deploy a suture in the tissue, and the suture is left in place after the coiled needle is withdrawn. The medical devices of the present disclosure thereby enable the closure of an abnormality such as a PFO while reducing the amount of material implanted in the body, compared to known devices.

As described further herein, the devices and methods of the present disclosure have varying implementations, such that the devices and methods are useable to close many different types of PFOs.

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

It is understood that the use of the term "target site" is not meant to be limiting, as the medical device may be configured to treat any target site, such as any vascular abnormality, a vessel, an organ, an opening, a chamber, a channel, a hole, a cavity, or the like, located anywhere in the body.

The term "vascular abnormality," as used herein is not meant to be limiting, as the medical device may be configured to treat a variety of vascular abnormalities. Furthermore, the term "lumen" is also not meant to be limiting, as the vascular abnormality may reside in a variety of locations within the vasculature, such as a vessel, an artery, a vein, a passageway, an organ, an organ wall (e.g., an atrial septal wall), a cavity, or the like. For ease of explanation, the examples used herein refer to the closure of a patent foramen ovale, or PFO, as described herein.

The term "distal" as used herein, is a broad term and is used in its ordinary sense, including, without limitation, as in the direction away from a user of a device; distal refers to a part of a device that is farther from an operator or user at any given time. The term "proximal" as used herein, is a broad term and is used in its ordinary sense, including, without limitation, as toward the user of the device; proximal refers to a part of a device that is closest to an operator or user.

The present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

FIG. 1 illustrates an example PFO 50 in a human heart. More specifically, in a normal heart, the septum secundum of the right atrium and the septum primum of the left atrium are fused together at birth, thus forming a fossa ovalis. In contrast, as shown in FIG. 1, a PFO 50 (i.e., unformed fossa ovalis) in an open configuration is depicted. The septum secundum 52 of the right atrium 54 and the septum primum 56 of the left atrium 58 overlap with one another but are not fused together. During contraction/beating of the heart, the unformed fossa ovalis flaps open and shut, creating a PFO tunnel 60 through the PFO 50 that allows unwanted blood flow between the left and right atrial chambers (58 and 54).

Figure 2:
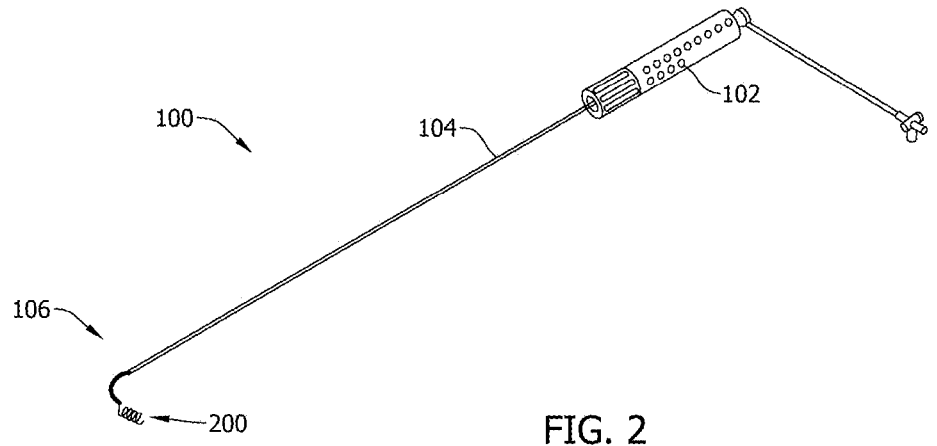
FIG. 2 is a schematic view of an exemplary embodiment of a delivery system for deploying a medical device.

FIG. 2 is a schematic diagram of a delivery system 100. Delivery system 100 includes a delivery device 102, such as a manifold or handle, that includes or is coupled to a delivery catheter 104 and a delivery cable 106 for deployment of a medical device 200 (not shown to scale) at a target site. Delivery system 100 may advantageously be a curved, and/or steerable device delivery system, including a curved and/or steerable catheter 104 and/or delivery cable 106. Such embodiments enable more precise delivery and deployment of the medical devices disclosed herein.

Figures 3A, 3B, 3C, 3D, 3E:
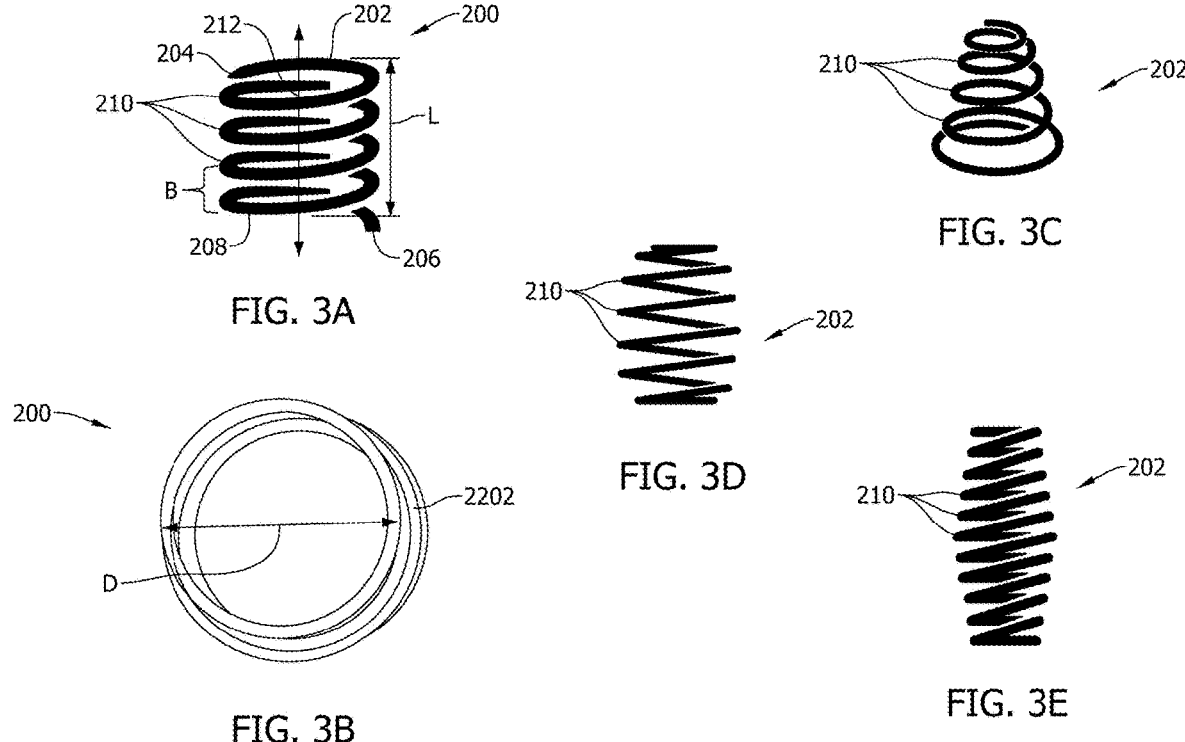
FIGS. 3A and 3B depict a side view and a top view, respectively, of a first embodiment of a medical device.
FIGS. 3C-3E depict alternative embodiments of the medical device.

Turning to FIGS. 3A and 3B, a first embodiment of a medical device 200 is depicted in a side view and a top view, respectively. Medical device 200 is embodied as a coil 202, also referred to herein as a coiled, spiral, or helical needle or implant. Coil 202 has a first end 204 and a second end 206, and a body 208 extending therebetween. At least one of first end 204 and second end 206 is a sharp point, such that coil 202 can function as a needle to puncture tissue when the sharp end(s) thereof is/are engaged with the tissue. Body 208 includes one or more "turns" 210 or complete revolutions of a circumference, between first and second ends 204, 206. In various embodiments described herein, body 208 advantageously includes more than one turn 210 and up to ten turns 210, with about 4 turns in one or more exemplary embodiments. Notably, body 208 may not necessarily include an integer number of turns 210, but can include, for example, 1.1, 1.25, 1.5, 1.75, etc. turns 210.

Turns 210 of coil 202 revolve or loop concentrically around a longitudinal axis 212. Coil 202 has a length L, measured between first and second ends 204, 206 and parallel to this longitudinal axis 212. In various embodiments, length L is between about 5 mm and about 12 mm.

In the embodiments of coil 202 depicted in FIGS. 3A and 3B, each turn has a same diameter D, which can also be referred to as the diameter D of coil 202. In various embodiments, diameter D is between about 2 mm and about 8 mm. Other embodiments of designs of coil 202 are shown in FIGS. 3C-3E. In these embodiments, turns 210 of the respective coil 202 do not all have a same diameter D. Rather, the diameter of turns 210 varies. In some of these embodiments, when coil 202 is deployed (as described further herein), the varying diameters of turns 210 enables certain smaller turns 210 to "nest" within adjacent, larger turns 210. This nesting can draw the adjacent tissue further together, enhancing the sealing effect provided by the deployed coil 202.

Additionally, coil 202 is formed such that a distance B between each turn 210 is the same and is known. Distance B may also be referred to as a "pitch" of coil 202 or turns 210. In some cases, therefore, the length L is equal to the number of turns 210 multiplied by the distance B between each turn 210. Notably, the particular distance B between turns 210 can vary between implementations of coil 202, as illustrated with respect to FIGS. 3A-3E. The specific length L and diameter D of coil 202 can be selected and implemented based on the characteristics of the tissue defect (e.g., PFO) to be closed using coil 202.

It should also be understood that the length L for coil 202 may be measured in an undeployed state, and the final length of coil 202 may be slightly less than or more than length L when coil 202 is deployed within the tissue. That is, coil 202 may be constructed of a rigid material, but may have some amount of elasticity or "give," which may result in coil 202 being stretched or otherwise reshaped somewhat during deployment thereof. In some instances, the length L of coil 202 may vary during delivery and deployment. For example, a delivery system (e.g., delivery system 100, shown in FIG. 2) may be configured to deliver coil 202 with a larger pitch, so the distance between turns 210 is larger than the original (e.g., heat-set) distance between turns 210. Therefore, once deployed, coil 202 will tend to bias back into its original configuration, thereby drawing the tissue closer together. That is, coil 202 may be constructed of a shape-memory material that tends to return to its original (e.g., heat-set) configuration. In the example embodiments of the present disclosure, coil 202 is formed from a material such as Eligiloy™, MP35, nitinol, a spring steel, or other similar material. In other embodiments, coil 202 may be formed from a polymeric material, such as nylon, PLA, PLGA, or other polymeric material, including shape memory polymeric materials.

Figure 4:
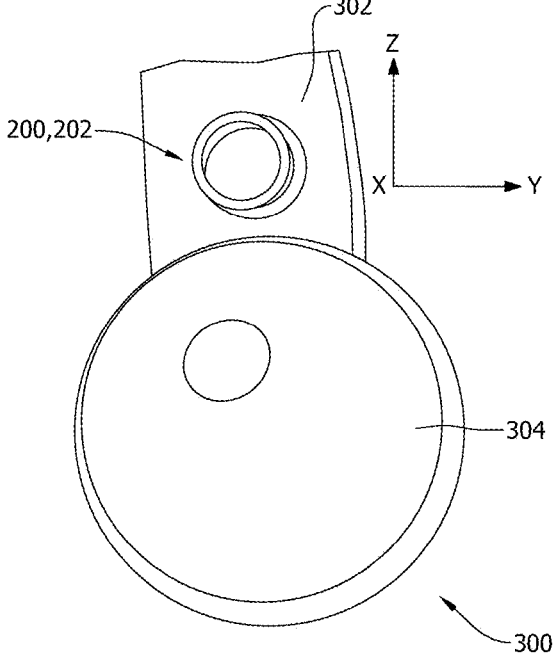
FIG. 4 depicts the medical device shown in FIGS. 3A and 3B deployed through a simulated PFO.

FIG. 4 illustrates a simulation of a PFO 300. More particularly, simulated PFO 300 includes a PFO tunnel 302, which is representative of PFO tunnel 60 shown in FIG. 1. Simulated PFO tunnel 302 includes two layers of material (simulating the tissue of the septum primum 56 and septum secundum 52) separated by a gap (not shown in FIG. 4), as in an actual (e.g., not simulated) PFO. Simulated PFO 300 also includes a pocket 304 on the "left atrial" side of simulated PFO tunnel 302, which may reasonably simulate an atrial septal aneurysm (ASA). Simulated PFO 300, in its initial state, permits the flow of liquid through simulated PFO tunnel 302. Therefore, simulated PFO 300 can be used to test or simulate various closure or sealing devices or methods, to evaluate a general level of efficacy thereof.

In the specific illustration of FIG. 4, coil 202 has been deployed through simulated PFO tunnel 302, along a direction generally parallel to the X direction (shown also in FIG. 1), which intersects the simulated tissue of the septum primum and septum secundum. This embodiment of deployment of coil 202, generally parallel to the X direction, may be referred to as a deployment of coil 202 "through" a PFO tunnel (e.g., PFO tunnel 60, as shown in FIG. 1). Coil 202 has been deployed through both layers of material of simulated PFO tunnel 302 (e.g., simulating deployment through both the septum primum 56 and the septum secundum 52) to couple the two layers of material together and close simulated PFO tunnel 302. Testing performed with coil 202 deployed through simulated PFO tunnel 302 as shown in FIG. 4 was generally successful at blocking flow through simulated PFO tunnel 302.

Accordingly, it can be understood that coil 202 can be used in the anatomy of a human patient (or another animal patient). In such cases, coil 202 would be advanced to PFO 50 and deployed through PFO tunnel 60 generally parallel to the X direction. First end 204 of coil 202 may be engaged against septum secundum 52. First end 204 would puncture septum secundum 52, and coil 202 would be rotated in the coiled direction of turns 210. The rotational motion would advance coil 202 longitudinally through septum secundum 52, until first end 204 of coil 202 passes through septum secundum 52 and into engagement with septum primum 56. Coil 202 would be further rotated to advance coil 202 longitudinally through septum primum 56.

In some embodiments, coil 202 is rotated until first end 204 is advanced entirely through septum primum 56 (e.g., into the left atrium 58). In other embodiments, coil 202 is rotated such that first end 204 terminates within the tissue of septum primum 56. In either case, second end 206 of coil 202 may terminate within the tissue of septum secundum 52 or may extend into the right atrium 54. In the final position of coil 202, body 208 extends at least partially through septum secundum 52 and septum primum 56.

The final position of coil 202, including first end 204 and second end 206, depends on many factors, including the length L of coil 202, a number of turns 210 of coil 202, and the thickness of septum primum 56 and/or septum secundum

52. In operation, each of these parameters is known, and the length L of coil 202 is selected to generally correspond to a thickness of the septum secundum 52 and the septum primum 56, taken along the X direction. A physician performing the deployment procedure would impose a known number of rotations on coil 202 (after first end 204 is engaged with the tissue) to ensure the desired final position of coil 202.

Figure 5:
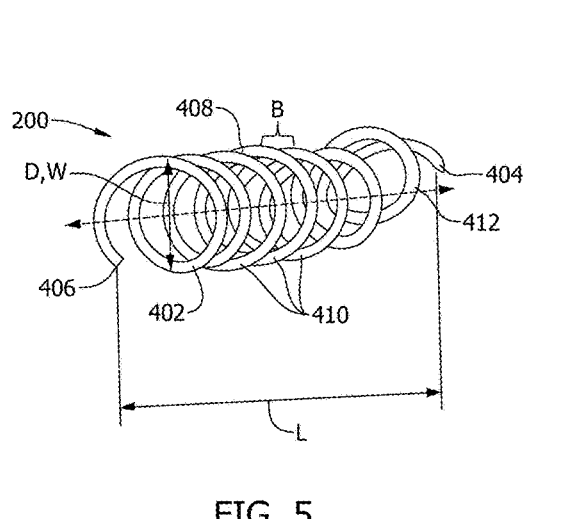
FIG. 5 depicts a perspective view of a second embodiment of a medical device.

Turning now to FIG. 5, another embodiment of medical device 200 is shown, in which medical device 200 is embodied as a flattened coil 402 or as a flattened coiled, spiral, or helical needle or implant. Like coil 202, flattened coil 402 includes a first end 404 and a second end 406, and a body 408 extending therebetween. At least one of first end 404 and second end 406 is a sharp point, such that coil 402 can function as a needle to puncture tissue when the sharp end(s) thereof is/are engaged with the tissue. Body 408 includes one or more turns 410 between first and second ends 404, 406. In various embodiments described herein, body 408 advantageously includes between three and ten turns 410, including eight turns 410. Notably, body 408 may not necessarily include an integer number of turns 410, but can include, for example, 4.1, 4.25, 4.5, 4.75, etc. turns 410.

With respect to flattened coil 402, turns 410 are not concentric around a longitudinal axis 412, as flattened coil 402 is "flattened" in a longitudinal direction, such that the turns 410 of body 408 only partially overlap one another along longitudinal axis 412. Stated differently, each turn 410 defines a hypothetical plane, and the plane of each turn 410 partially overlaps a plane of an adjacent turn 410. The distance B between turns 410 is reduced or compressed, relative to, for example, a coil 202 (as shown in FIG. 3A). Coil 402 has a length L measured between first and second ends 404, 406, or between first end 404 and a point the furthest therefrom along the longitudinal axis 412 (e.g., where second end 406 is part of a partial turn 410 that overlaps with a preceding turn 410). In various embodiments, length L is between about 5 mm and about 15 mm. Each turn 410 has a same diameter D, which can also be referred to as a width W of coil 402. In various embodiments, diameter D and/or width W is between about 2 mm and about 5 mm. The specific length L and width W of coil 402 can be selected and implemented based on the characteristics of the tissue defect (e.g., PFO) to be closed using coil 402.

It should also be understood that the length L for coil 402 may be measured in an undeployed state, and the final length of coil 402 may be slightly less than or more than length L when coil 402 is deployed within the tissue. That is, coil 402 may be constructed of a rigid material, but may have some amount of elasticity or "give," which may result in coil 402 being stretched or otherwise reshaped somewhat during deployment thereof. In some instances, the length L of coil 402 may vary during delivery and deployment. For example, a delivery system (e.g., delivery system 100, shown in FIG. 2) may be configured to deliver coil 402 with a greater pitch, so the distance between turns 410 is larger than the original (e.g., heat-set) distance between turns 410. In some specific instances, coil 402 may be delivered in a substantially round configuration, similar to coil 202 (shown in FIGS. 3A-3E). Once deployed, coil 402 will tend to bias back into its original configuration, thereby drawing the tissue closer together. That is, coil 402 may be constructed of a shape-memory material that tends to return to its original (e.g., heat-set) configuration. In the example embodiments of the present disclosure, coil 402 is formed from a material such as Eligiloy™, MP35, nitinol, a spring steel, or other similar material. In other embodiments, coil 402 may be formed from a polymeric material, such as nylon, PLA, PLGA, or other polymeric material, including shape memory polymeric materials.

Figure 6:
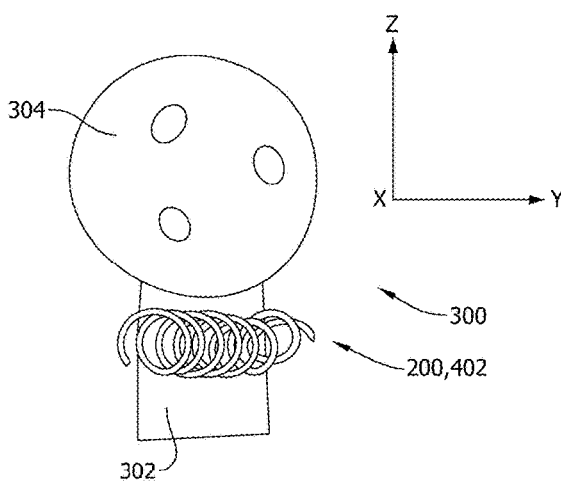
FIG. 6 depicts the medical device shown in FIG. 5 deployed across a simulated PFO.

FIG. 6 illustrates another simulation of a PFO, substantially similar to simulated PFO 300 shown in FIG. 4, and like numerals will be used to refer to like components. In the specific illustration of FIG. 6, coil 402 has been deployed across simulated PFO tunnel 302, along a direction generally parallel to the Y direction (also shown in FIG. 1). This embodiment of deployment of flattened coil 402, generally parallel to the Y direction, may be referred to as deployment of flattened coil 402 "across" a PFO tunnel (e.g., PFO tunnel 60, as shown in FIG. 1). Flattened coil 402 has been deployed through both layers of material of simulated PFO tunnel 302 (e.g., through both the septum primum and the septum secundum) to couple the layers of material together and close simulated PFO tunnel 302. Testing performed with flattened coil 402 deployed across simulated PFO tunnel 302 as shown in FIG. 6 was generally successful at blocking flow through simulated PFO tunnel 302.

Accordingly, it can be understood that flattened coil 402 can be used in the anatomy of a human patient (or another animal patient). In such cases, flattened coil 402 would be advanced to PFO 50 and deployed across PFO tunnel 60 generally parallel to the Y direction. More specifically, first end 404 of flattened coil 402 would be engaged with and puncture tissue of septum secundum 52. Flattened coil 402 would be oriented generally parallel to the Y direction, or angled slightly towards left atrium 58, and rotated in the coiled direction of turns 410. The rotational motion would advance flattened coil 402 generally in the Y direction, and first end 404 would advance through septum secundum 52 into septum primum 56 during rotation of flattened coil 402. Coil 402 would be further rotated to advance coil 402 longitudinally across PFO tunnel 60, and first end 404 would iteratively and alternatingly puncture and advance through each of septum secundum 52 and septum primum 56. Body 408 of coil 402 would be embedded into the tissue of septum secundum 52 and septum primum 56 facing PFO tunnel 60.

Flattened coil 402 is rotated until first end 404 is advanced a desired distance across PFO tunnel 60. Specifically, the length L of flattened coil 402 is selected to approximate a width of the PFO tunnel 60, and a physician performing the deployment procedure would impose a known number of rotations on flattened coil 402 (after first end 404 is engaged with the tissue) to ensure the desired final position of flattened coil 402 across substantially the entire width of PFO tunnel 60.

In some embodiments, a non-flattened coil (e.g., a coil similar to coil 202) may be implemented in a deployment across a PFO tunnel. In such cases, the above explanation of deployment of such a coil is substantially the same. Throughout the following discussions, reference to a "coil" may refer equally to a non-flattened coil, such as coil 202, and to a flattened coil, such as flattened coil 402. Accordingly, further reference is made to a coiled needle, which encompasses both a non-flattened coil and flattened coil.

Figure 7:
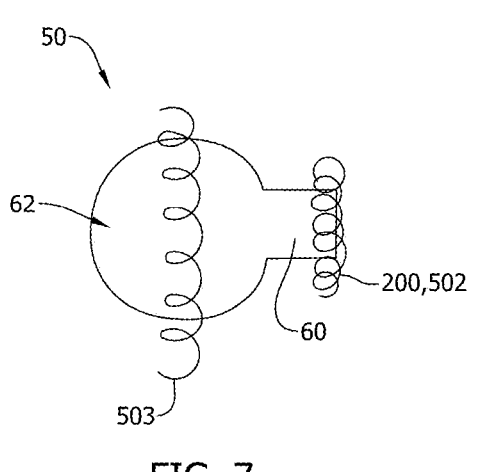
FIG. 7 illustrates a plurality of medical devices in accordance with the present disclosure, one medical device being deployed across a PFO in a first position and another medical device being deployed across an atrial septal aneurysm adjacent the PFO.
Figure 8:
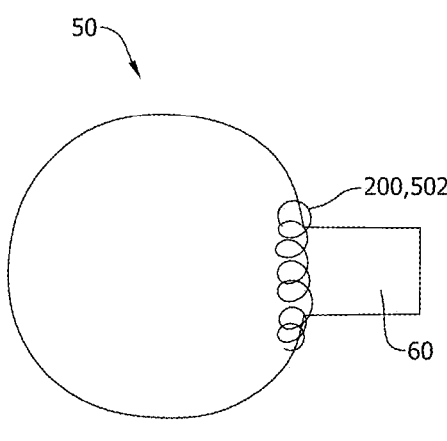
FIG. 8 depicts the medical device deployed across the PFO shown in FIG. 7, the medical device being deployed across the PFO in a second position.

Turning to FIGS. 7 and 8, alternative embodiments of deployment of a medical device 200 including one or more coiled needles across a PFO (e.g., PFO 50, shown in FIG. 1) are depicted. Specifically, in FIG. 7, a coiled needle 502 is deployed across the PFO tunnel (e.g., PFO tunnel 60, shown in FIG. 1) in a first position, adjacent to a first end of PFO tunnel 60. Additionally, a second coiled needle 503 is deployed across an adjacent atrial septal aneurysm (ASA) 62. This second coiled needle 503 may facilitate reducing movement of the ASA 62 as the patient's heart beats, by securing looser or more "floppy" tissue against tissue of the septal wall. With respect to FIG. 8, a coiled needle 502 is deployed across PFO tunnel 60 in a second position, adjacent to a second end-opposite the first end—of PFO tunnel 60. The particular position of coiled needle 502 relative to PFO tunnel 60 may be selected by a physician and may depend on the characteristics of the PFO 50 to be closed.

Figure 9:
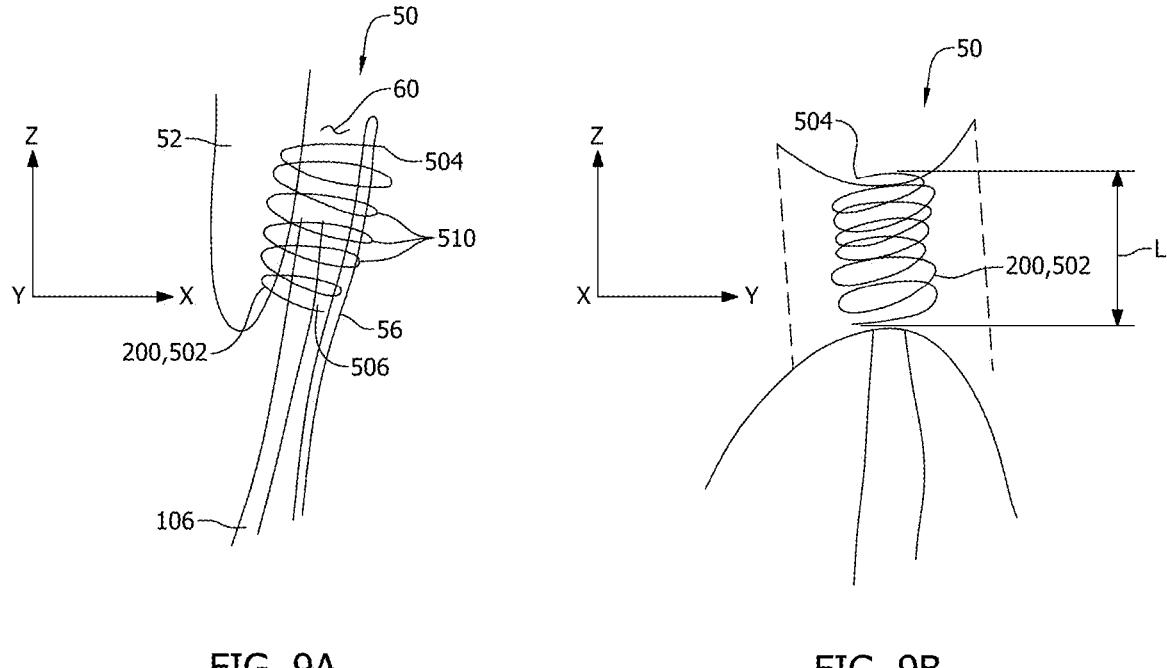
FIGS. 9A and 9B schematically depict two side views of a medical device deployed along a PFO tunnel.

With reference now to FIGS. 9A and 9B, another embodiment of deployment of a medical device 200 including coiled needle 502 to close a PFO (e.g., PFO 50, shown in FIG. 1) is depicted from two sides. In this embodiment, coiled needle 502 is deployed through PFO tunnel 60 (e.g., using delivery cable 106, shown in FIG. 2), along a direction generally parallel to the Z direction. This embodiment of deployment of a coiled needle 502, generally parallel to the Z direction and between septum primum 56 and septum secundum 52, may be referred to as deployment of coiled needle 502 "along" the PFO tunnel 60. In this embodiment, coiled needle 502 is embedded in the tissue of both the septum primum 56 and septum secundum 52 facing the PFO tunnel 60.

To facilitate deployment along PFO tunnel 60, coiled needle 502 would be advanced to PFO 50 and between the two layers of tissue at a first end of the PFO tunnel 60. A first end 504 of coiled needle 502 would be engaged with and puncture tissue of one of the septum secundum 52 and septum primum 56. Coiled needle 502 would be oriented generally parallel to the Z direction and rotated in the coiled direction of turns 510 thereof. The rotational motion would advance coiled needle 502 generally in the Z direction, and first end 504 would iteratively and alternatingly puncture and advance through each of septum secundum 52 and septum primum 56. The body of coiled needle 502 would be embedded into the tissue of septum secundum 52 and septum primum 56 facing PFO tunnel 60.

Coiled needle 502 is rotated until first end 504 is advanced a desired distance along PFO tunnel 60. Specifically, a length L of coiled needle 502 (shown in FIG. 9B) is selected to approximate a length of the PFO tunnel 60, and a physician performing the deployment procedure would impose a known number of rotations on coiled needle 502 (after first end 504 is engaged with the tissue) to ensure the desired final position of coiled needle 502 along substantially the entire length of PFO tunnel 60.

It should be understood that two or more coils or flattened coils can be deployed relative to a single PFO without departing from the scope of the present disclosure, including in any of the deployment embodiments described herein. For example, a first coil and a second coil can be deployed through a PFO, where a first coil is adjacent a first end of the PFO tunnel, and a second coil is adjacent a second end of the PFO tunnel. As another example, a first coil or flattened coil and a second coil or flattened coil can be deployed across a PFO, where the first coil/flattened coil is adjacent the first end of the PFO tunnel, and the second coil/flattened coil is adjacent the second end of the PFO tunnel. Such implementations may facilitate improved sealing at both ends of the PFO tunnel.

In any of the above embodiments, coiled needle 502 (which may include coil 202 and/or flattened coil 402) is deployed into the tissue of the PFO 50 and remains in place after deployment thereof. In such embodiments, the coiled needle functions to close the PFO tunnel and keep the PFO tunnel in the closed state. Thereby, the coiled needle enables sealing of the PFO.

It is further contemplated that in any of the embodiments discussed herein, the coiled needle may have suture material coupled thereto, and the coiled needle may function as a delivery component to deliver and deploy the suture material. In these embodiments, as discussed further below, the suture is deployed and de-coupled from the coiled needle, and remains in place, and the coiled needle is withdrawn from the patient. The suture functions to close the PFO and keep the PFO tunnel in the closed state, and as such, the suture enables sealing of the PFO.

Figure 10:
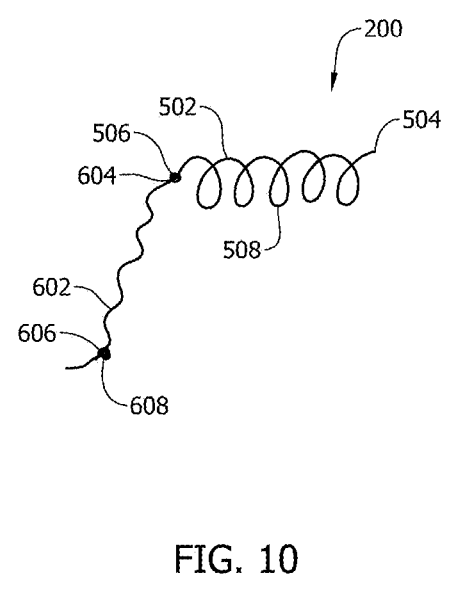

FIG. 10 is a simplified diagram of a medical device 200 embodied as a coiled needle 502 (e.g., a flattened or non-flattened coil) with a suture 602 coupled thereto. Coiled needle 502 includes first end 504 and a second end 506, and a body 508 extending therebetween. Suture 602 is coupled to second end 506 of coiled needle 502 at a distal end 604 of suture 602. A proximal end 606 of suture 602 includes a knot 608.

Figure 11:
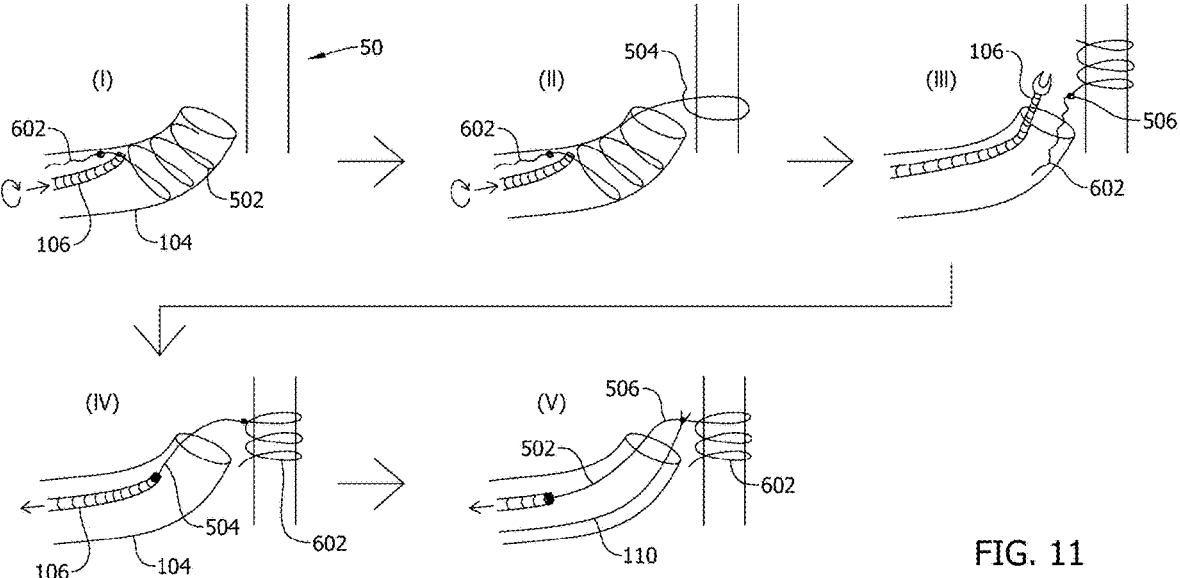
FIG. 11 illustrates a method of closing a PFO using the medical device shown in FIG. 10.

A more detailed schematic diagram of deployment of suture 602 to close a PFO (e.g., PFO 50), using coiled needle 502 as a delivery component, is shown in FIG. 11. As shown, in Step (I), coiled needle 502 is advanced to PFO 50 using delivery catheter 104 (shown in FIG. 2). Coiled needle 502 and suture 602 are retained in a delivery configuration within a lumen of delivery catheter 104 as delivery catheter 104 is advanced to the PFO 50, and delivery cable 106 is used to push coiled needle 502 distally out of delivery catheter 104. As shown in Step (II), first end 504 of coiled needle 502 is engaged with tissue at the PFO 50 (e.g., the septum secundum) and is rotated, using delivery cable 106, to advance coiled needle 502 into the tissue and out of the delivery catheter 104. As coiled needle 502 moves, suture 602 is drawn behind it. Coiled needle 502 may be deployed through, across, or along the PFO 50, as described herein, and may adopt a deployed configuration.

Once coiled needle 502 is fully advanced out of delivery catheter 104 and into the tissue, delivery cable 106 is detached from second end 506 of coiled needle 502, as shown in Step (III). Delivery cable 106, or another cable component, is reattached to coiled needle 502 at first end 504, such that coiled needle 502 can be pulled through the tissue, as shown in Step (IV), until coiled needle 502 is fully beyond the tissue, as shown in Step (V). In the example embodiment, coiled needle 502 is drawn back into delivery catheter 104. Suture 602 is drawn behind coiled needle 502 and through the tissue, until knot 608 engages with the tissue or, in other embodiments, a sufficient length of suture is determined to have been drawn through the tissue. As also shown in Step (V), a cutting tool 110 is advanced through the lumen of delivery catheter 104 and is used to cut suture 602 adjacent to second end 506 of coiled needle 502. Suture 602 remains in place, and coiled needle 502 is withdrawn from the patient via delivery catheter 104.

Although this option is discussed with particularity in reference to FIG. 11, it should be understood that the option of the suture may be implemented in any of the deployment embodiments discussed above. For example, with respect to FIG. 4, coil 202 may have a suture (e.g., suture 602) coupled to second end 206 thereof. Coil 202 is deployed through a PFO tunnel (e.g., PFO tunnel 60, shown in FIG. 1) as described above. However, coil 202 is advanced further, via the same rotational motion, until coil 202 is fully located beyond the PFO tunnel, such that second end 206 of coil 202 is advanced out of the tissue of the septum primum. The suture coupled to coil 202 travels the same rotational path through the PFO tunnel. The end of the suture coupled to coil 202 is cut, coil 202 is removed, and the suture remains in place through the PFO tunnel.

As another example, with respect to FIG. 6, flattened coil 402 may have a suture (e.g., suture 602) coupled to second end 406 thereof. Flattened coil 402 is deployed across a PFO tunnel (e.g., PFO tunnel 60, shown in FIG. 1) as described above. However, flatted coil 402 is advanced further, via the same rotational motion, until flattened coil 402 is fully located beyond the PFO tunnel, such that second end 406 of flattened coil 402 is advanced out of the tissue of the septum secundum and the septum primum. Advantageously, flattened coil 402 is advanced out of the septal tissue on a same side of the PFO as it entered the septal tissue (e.g., a right atrial side) to simplify withdrawal of flattened coil 402. The suture coupled to flattened coil 402 travels the same rotational path across the PFO tunnel. The end of the suture coupled to flattened coil 402 is cut, flattened coil 402 is removed, and the suture remains in place across the PFO tunnel.

As another example, with respect to FIGS. 7 and 8, a suture (e.g., suture 602) can be deployed using coiled needle 502/503 at any location across the PFO tunnel (e.g., at either end of the PFO tunnel) and/or across an ASA adjacent to the PFO.

As a further example, with respect to FIGS. 9A and 9B, coiled needle 502 may have a suture (e.g., suture 602) coupled to second end 506 thereof. Coiled needle 502 is deployed along a PFO tunnel 60 as described above. However, coiled needle 502 is advanced further, via the same rotational motion, until coiled needle 502 is fully located beyond the PFO tunnel 60, such that second end 506 of coiled needle 502 is advanced out of the tissue of the septum secundum and the septum primum. The suture coupled to coiled needle 502 travels the same rotational path along the PFO tunnel 60. The end of the suture coupled to coiled needle 502 is cut, coiled needle 502 is removed, and the suture remains in place along the PFO tunnel 60.

It is further contemplated that in any of the embodiments discussed herein, rather than deploying a solid coiled needle (e.g., formed from a solid wire material), a coiled tube may be used. The coiled tube is hollow and can function as a closure component or a delivery component for a suture delivery system. More specifically, in some such embodiments, the coiled tube is deployed (using a guide component, in some instances) and remains in place, and the coiled tube functions to close the PFO and keep the PFO in the closed state, thereby enabling sealing of the PFO. Alternatively, the coiled tubed is a delivery component for a suture retained therein. In such cases, the suture is deployed and remains in place, and the coiled tube is withdrawn from the patient. The suture functions to close the PFO and keep the PFO tunnel in the closed state, and as such, the suture enables sealing of the PFO.

Figure 12:
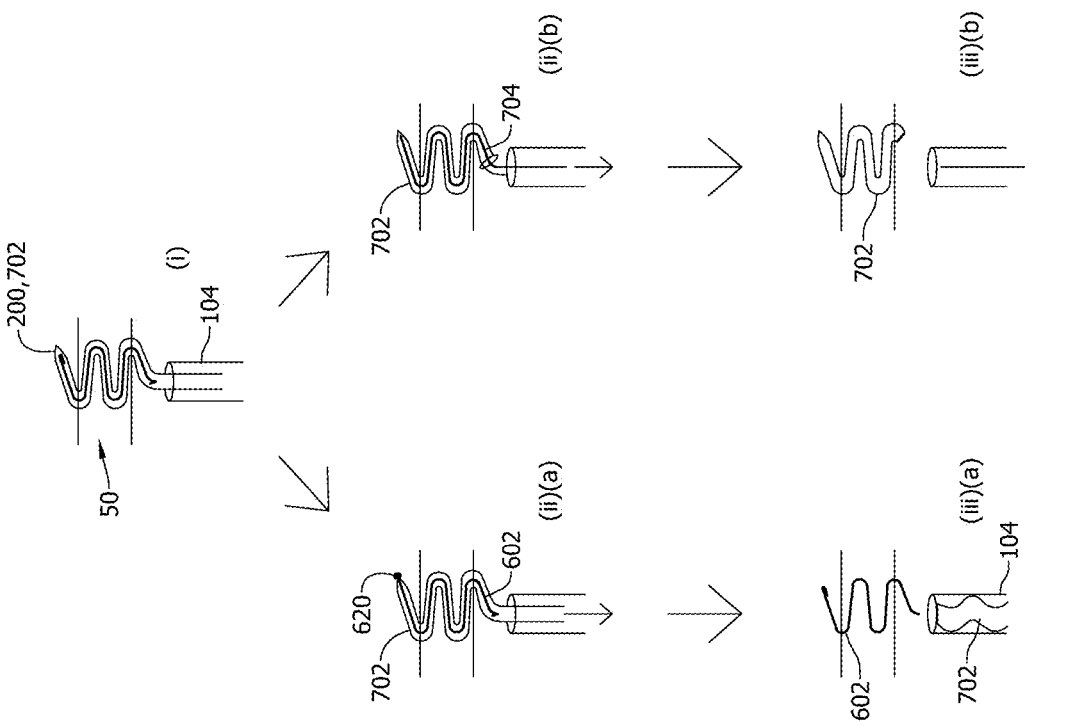
FIG. 12 illustrates another method of closing a PFO using a medical device or suture delivery system including a spiral tube and a suture.

A schematic diagram of deployment of a medical device 200 including a coiled tube 702 is shown in FIG. 12. In Step (i), coiled tube 702 is advanced to the PFO 50 and through the tissue thereof (e.g., the septum secundum and the septum primum), using delivery catheter 104 (shown in FIG. 2) and, in some cases, delivery cable 106 (also shown in FIG. 2) or another guide component (e.g., a polymer core 704). Coiled tube 702 may be deployed through, across, or along the PFO 50, as described herein. In the example embodiment, coiled tube 702 has a tapered or otherwise pointed or sharp end, such that coiled tube 702 can puncture and advance through the tissue of the PFO 50.

In Step (ii) (a), coiled tube 702 is shown as retaining suture 602 therein. Suture 602, in this embodiment, includes an anchoring component 620 at the distal end 604 (see FIG. 10) thereof. Anchoring component 620 may be embodied as a "fishhook" or other mechanism that expands once distal end 604 is advanced out of coiled tube 702. Anchoring component 620 secures distal end 604 of suture 602 against the tissue as coiled tube 702 is rotated in an opposing direction and withdrawn from the PFO 50. Thereby, suture 602 remains in place to close the PFO 50, as depicted in Step (iii) (a).

In Step (ii) (b), by contrast, coiled tube 702 is shown as retaining polymer core 704 therein, which may function as a guide component to advance coiled tube 702 out of delivery catheter 104 and/or through the tissue. Once coiled tube 702 is fully deployed, polymer core 704 is withdrawn back into delivery catheter 104, and coiled tube 702 remains in place to close the PFO 50, as depicted in Step (iii) (b).

Although this option of using a hollow coiled tube, as a delivery component for a suture or as a device to close a PFO, is discussed with particularity in reference to FIG. 12, it should be understood that the hollow coiled tube may be implemented in any of the deployment embodiments discussed above.

In any embodiment of the present disclosure, delivery device 102 can be configured to allow manipulation (e.g., deflection in a proximal or distal direction) of either the septum secundum or the septum primum, for example, to facilitate positioning the medical device 200 in any desired position relative to the septum secundum and/or the septum primum. Moreover, in any embodiment of the present disclosure, delivery catheter 104 of the delivery system 100 may have any suitable size that enables medical device 200 and delivery system 100 to function as described herein. In some embodiments, the outer diameter of delivery catheter 104 is about 8-12 French.

In some embodiments, a medical device in accordance with the present disclosure (e.g., a coil, flattened coil, coiled needle, coiled tube, etc.) is formed in its entirety of a thin wire material such as single strand wire, multistrand wire, braided wire, wound wire ribbon, etc. In embodiments comprising wound wire ribbon, a flat and wide, yet thin, wire material is formed. In other embodiments, the medical device may be formed in its entirety from a laser-cut material. In some embodiments, the medical device may be formed from a metallic material, such as nitinol, Eligiloy™, MP35, stainless steel, and the like. In some embodiments, the medical device may be formed from a non-metallic (e.g., polymeric) material, such as Nylon, PEBAX™, bioabsorbable Poly (L-lactide) (PLLA), poly(lactic-co-glycolic acid) (PLGA) Magnesium. In some embodiments, the material is a shape-memory material.

Where present, the suture may be formed from one or more suture materials, including bioabsorbable or non-bioabsorbable materials, such as a polyester or other polymeric material.

In some embodiments, the medical device—that is, the coiled needle—is textured, and/or includes divots or other features that increase the frictional force of retention of the medical device against the tissue, which may prevent the coil from moving (e.g., backing out) after being deployed in vivo.

In some embodiments, the medical device (e.g., a coil, flattened coil, coiled needle, coiled tube, etc.) includes one or more attachment features (not shown) at one end thereof (e.g., the second end), which enables coupling delivery cable 106 to medical device 200, for deployment of medical device 200 at the target site. Additionally or alternatively, delivery cable 106 includes one or more attachment features, such as clasps, that enable coupling delivery cable 106 to medical device 200 without impacting the structure of medical device 200. Attachment features may be embodied as, for example, a threaded connection between the medical device 200 and the delivery cable 106, or a hook and eyelet configuration. The attachment features of the medical device 200 and/or delivery cable 106 also enable a secure enough coupling therebetween, such that delivery cable 106 can be used to rotate medical device 200 to advance medical device 200 through tissue at the PFO.

While embodiments of the present disclosure have been described, it should be understood that various changes, adaptations, and modifications may be made therein without departing from the spirit of the disclosure and the scope of the appended claims. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. It is intended that all matter contained in the above description or shown in the accompanying drawings shall be interpreted as illustrative only and not limiting. Changes in detail or structure may be made without departing from the spirit of the disclosure as defined in the appended claims.

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments described and that modifications and other embodiments are intended to be included within the scope of the appended claims. Although specific terms are employed herein, they are used in a generic and descriptive sense only and not for purposes of limitation.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method of closing a patent foramen ovale (PFO), the method comprising:

advancing a coiled needle to a location adjacent to the PFO;

positioning a first end of the coiled needle against tissue adjacent to the PFO;

puncturing the tissue with the first end of the coiled needle; and

rotating the coiled needle to advance the coiled needle through tissue of both a septum primum and a septum secundum defining the PFO, wherein advancing the coiled needle to the location adjacent to the PFO comprises (i) retaining the coiled needle in a delivery configuration in a lumen of a delivery catheter, a pitch of the coiled needle in the delivery configuration being greater than a pitch of the coiled needle in a deployed configuration, (ii) positioning a distal end of the delivery catheter at the location, and (iii) advancing the coiled needle distally out of the distal end of the delivery catheter.

2. The method of claim 1, wherein a PFO tunnel is defined between the septum primum and the septum secundum, and wherein rotating the coiled needle to advance the coiled needle through the tissue comprises:

rotating the coiled needle to advance the coiled needle through the tissue of the septum secundum and the septum primum through the PFO tunnel in an X direction that intersects the septum secundum and the septum primum.

3. The method of claim 1, wherein a PFO tunnel is defined between the septum primum and the septum secundum, and wherein rotating the coiled needle to advance the coiled needle through the tissue comprises:

rotating the coiled needle to advance the coiled needle alternatingly through the tissue of the septum secundum and the septum primum, across the PFO tunnel in a Y direction.

4. The method of claim 1, wherein a PFO tunnel is defined between the septum primum and the septum secundum, and wherein rotating the coiled needle to advance the coiled needle through the tissue comprises:

rotating the coiled needle to advance the coiled needle alternatingly through the tissue of the septum secundum and the septum primum, along the PFO tunnel in a Z direction.

5. The method of claim 1, wherein a suture is coupled to a second end of the coiled needle, the method further comprising:

advancing the coiled needle beyond the tissue of the septum primum and septum secundum, said advancing drawing the suture through the tissue behind the coiled needle;

decoupling the suture from the coiled needle; and withdrawing the coiled needle, leaving the suture in place in the tissue.

6. The method of claim 1, further comprising coupling a delivery cable to a second end of the coiled needle, wherein advancing the coiled needle distally out of the distal end of the delivery catheter comprises advancing the delivery cable distally through the delivery catheter.

7. The method of claim 1, wherein the coiled needle includes a hollow coiled body defining a lumen therethrough, the method further comprising:

positioning a core within the coiled needle, advancing the core distally out of the distal end of the delivery catheter, and

withdrawing the core from the coiled needle, leaving the coiled needle in place in the tissue at the location.

8. A patent foramen ovale (PFO) closure system comprising:

a closure device comprising a body extending between a first end and a second end, the body having a coiled shape comprising more than one complete turn, wherein at least one of the first end or the second end is a sharp point configured to puncture tissue at a target site within anatomy of a patient; and a delivery device configured to deliver the closure device to the PFO, wherein the closure device has a delivery configuration in which the closure device is retained in a lumen of the delivery device, and a deployed configuration in which the closure device is not retained in the lumen of the delivery device, a pitch of the closure device in the delivery configuration being greater than a pitch of the closure device in the deployed configuration.

9. The PFO closure system of claim 8, wherein the closure device body comprises more than three complete turns.

10. The PFO closure system of claim 8, wherein each turn of the closure device body is concentric with each other turn of the body.

11. The PFO closure system of claim 8, wherein the closure device body is flattened such that a respective plane of each turn of the body only partially overlaps a plane of an adjacent turn.

12. The PFO closure system of claim 8, wherein the first end of the closure device is the sharp point, the PFO closure system further comprising a suture material coupled to the second end to the closure device.

13. A suture delivery system comprising:

a coiled tube comprising a hollow coiled body defining a lumen therethrough, a first end, and a second end, the first end comprising a sharp point configured to puncture tissue at a target site within anatomy of a patient; and a delivery catheter configured to advance the coiled tube to the target site, wherein the coiled tube has a delivery configuration in which the coiled tube is retained in a lumen of the delivery catheter, and a deployed configuration in which the coiled tube is not retained in the lumen of the delivery catheter, a pitch of the coiled tube in the delivery configuration being greater than a pitch of the coiled tube in the deployed configuration.

14. The suture delivery system of claim 13, further comprising a suture material within the lumen of the coiled tube.

15. The suture delivery system of claim 14, the suture material comprising an anchoring component at a distal end thereof.

16. The suture delivery system of claim 13, wherein the coiled tube is formed from a polymeric material.

* * * * *